United States Patent
Collier, Jr.

[11] Patent Number: 5,505,917
[45] Date of Patent: Apr. 9, 1996

[54] SOLAR HEAT EXCHANGER AND CONCENTRIC FEEDBACK TUBE SYSTEM FOR DISINFECTING WATER

[76] Inventor: Robert K. Collier, Jr., 109 Tequesta Harbor Dr., Merritt Island, Fla. 32952

[21] Appl. No.: 317,343

[22] Filed: Oct. 4, 1994

[51] Int. Cl.$^6$ .................................................. B01B 1/00
[52] U.S. Cl. .................. 422/307; 126/684; 126/694; 126/696; 210/183
[58] Field of Search .................. 126/263.07, 683, 126/684, 694, 696; 422/307, 38; 210/183, 185

[56] References Cited

U.S. PATENT DOCUMENTS

| | | | |
|---|---|---|---|
| 3,428,529 | 2/1969 | Gumucio | 159/1 |
| 3,441,482 | 4/1969 | Avery | 202/234 |
| 4,066,550 | 1/1978 | Beaumont | 219/183 |
| 4,098,264 | 7/1978 | Brokaw | 126/271 |
| 4,235,678 | 11/1980 | McKeen | 202/185 R |
| 4,253,307 | 3/1981 | Smith | 60/641 |
| 4,406,749 | 9/1983 | Wetzel | 202/234 |
| 4,550,712 | 11/1985 | Moravnik | 126/439 |
| 4,557,251 | 12/1985 | Burkhardt | 126/417 |
| 4,585,524 | 4/1986 | Hoiss | 203/11 |
| 4,610,298 | 9/1986 | van Schagen et al. | 105/39 |
| 4,988,484 | 1/1991 | Karkon | 422/186.19 |
| 5,053,110 | 10/1991 | Deutsch | 202/176 |
| 5,085,753 | 2/1992 | Sherman | 204/267 |
| 5,181,991 | 1/1993 | Deutsch | 202/176 |
| 5,281,310 | 1/1994 | Djelouah et al. | 202/185 |

*Primary Examiner*—Timothy M. McMahon
*Assistant Examiner*—N. Bhat
*Attorney, Agent, or Firm*—Brian S. Steinberger

[57] ABSTRACT

A concentric receiver tube for passing water to be disinfected twice before the aperture path of a concentric solar reflector. The novel receiver tube uses the water that is heated by the reflector to additionally pre-heat fresh incoming water to maximize the heat transfer exchange rate. The novel concentric tube receiver to preheat and disinfect water when the source of heat are combustion gases or catalyst beds. The maximum disinfecting temperature needs only be 90 C in order to create an instantaneous disinfection condition.

16 Claims, 5 Drawing Sheets

SOLAR HEAT EXCHANGER AND CONCENTRIC FEEDBACK TUBE SYSTEM FOR DISINFECTING WATER

This invention relates to techniques for disinfecting water, and in particular to a solar heat exchange method and concentric feedback tube apparatus for disinfecting water.

BACKGROUND AND PRIOR ART

The need for safe drinking water covers the entire world's population. Non-potable drinking water is a major problem for much of the world's population. It has been estimated that approximately 15 to 20 million children under the age of 5 die from diarrheal conditions brought on by infected drinking water every year. This is equivalent to a fully-loaded DC-10 crashing every ten minutes of every day, 365 days a year Heat is one of the most effective methods of disinfecting drinking water. Contrary to popular opinion, boiling water for many minutes or even hours is not necessary to successfully disinfect. Numerous investigations have been conducted to demonstrate that temperatures much lower than the sea level boiling point (100 C) can successfully disinfect drinking water. Heat inactivation of microorganisms is exponential with time. In general, disinfection times can range from instantaneous at 90 C to 20 minutes at 55 C Using conventional means of heating water such as heating water over an open-flamed stove, results in an extremely energy-intensive process where as much as 1500 BTU per gallon of water can be required. In general, heating water from an ambient temperature to at least a 90 C disinfection temperature requires a minimum energy input of approximately 130 BTU/lb of water. This energy is usually wasted because once the disinfection temperature is reached, and the water is now safe to drink, the heat content of the water is dissipated to the environment before consummation.

Chlorine is considered the most well known technique for disinfecting drinking water. However, chlorine is a toxin that must constantly be replenished in order to be effective. As a replenishable chemical, there is always a continuing cost incurred.

Other techniques of disinfection such as membranes, resin beds, and the like, require electricity for operation. This source of energy may not be available at the site or would be too expensive when compared to this invention.

Thus, the need exists for a safe and inexpensive technique for disinfecting drinking water.

SUMMARY OF THE INVENTION

The first objective of the present invention is to provide a non chemical method for disinfecting water.

The second object of this invention is to provide a continuous non-toxic method for disinfecting water.

The third object of this invention is to provide a simple method for disinfecting water.

The fourth object of this invention is to provide an efficient method for disinfecting water.

The fifth object of this invention is to provide a reliable method for disinfecting drinking water.

The sixth object of this invention is to provide an easy-to-operate method for disinfecting drinking water.

The seventh object of this invention is to provide totally self-contained method for disinfecting water.

The eighth object of this invention is to provide a feedback concentric tube system for heating water to disinfecting temperatures.

Further objects and advantages of this invention will be apparent from the following detailed description of a presently preferred embodiment which is illustrated schematically in the accompanying drawings.

DESCRIPTION OF THE PREFERRED EMBODIMENT

Before explaining the disclosed embodiment of the present invention in detail it is to be 10 understood that the invention is not limited in its application to the details of the particular arrangement shown since the invention is capable of other embodiments. Also, the terminology used herein is for the purpose of description and not of limitation.

First Preferred Embodiment

Figure 1:
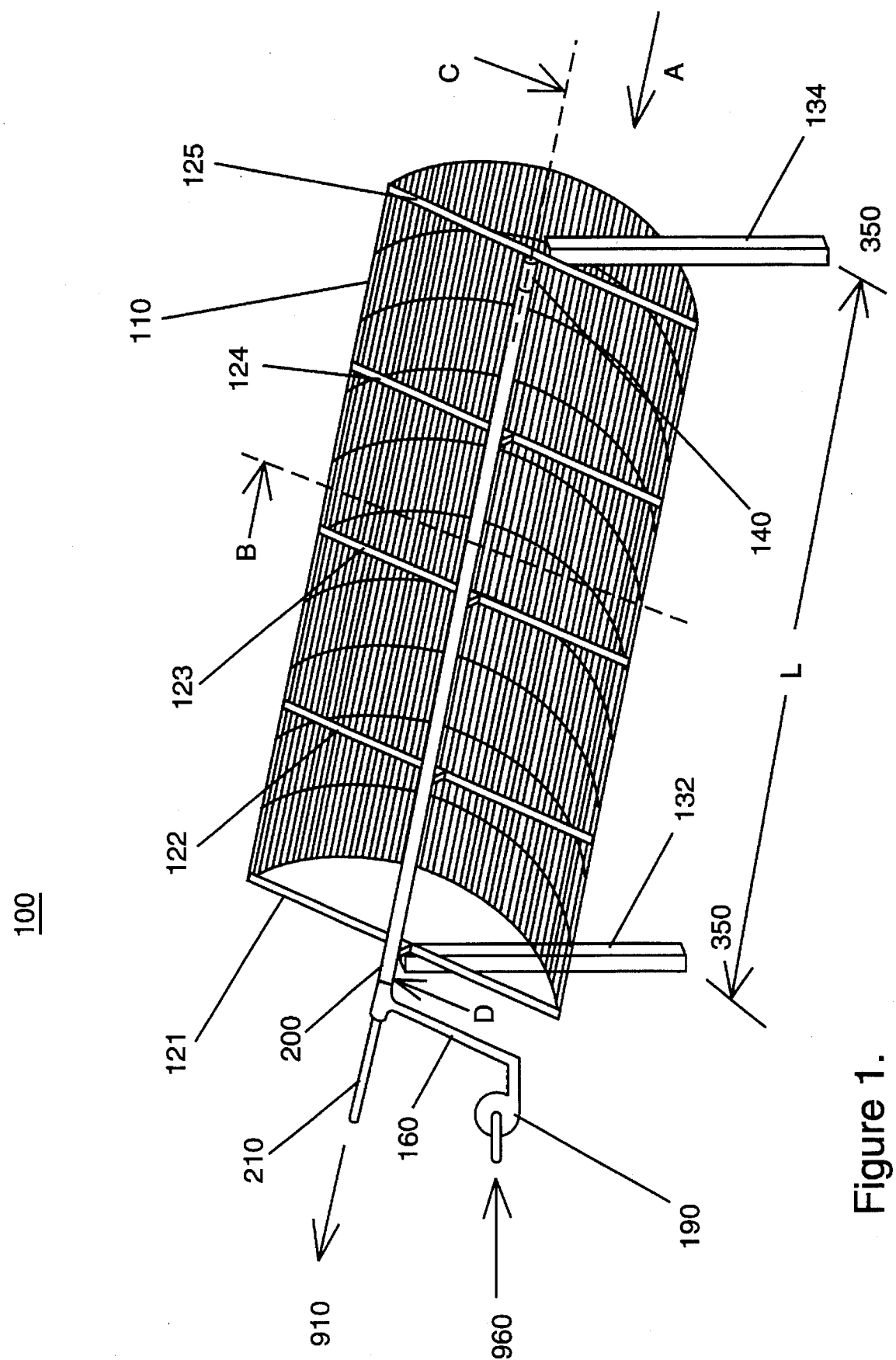
FIG. 1 shows an external rear view of the overall invention including the parabolic concentrator reflector along with the novel counterflow heat exchanger receiver tube.
Figure 2:
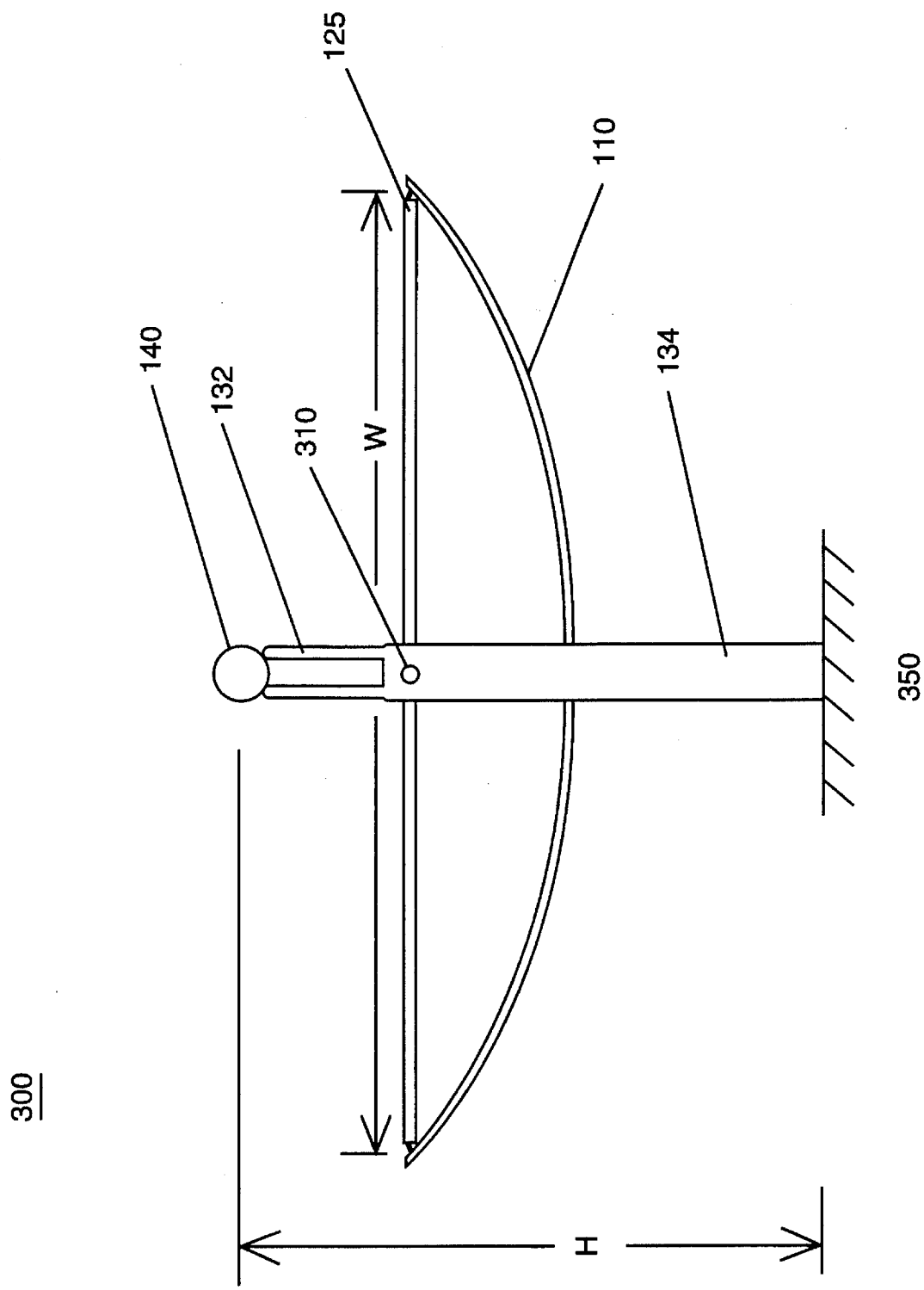
FIG. 2 shows a end view of the invention of FIG. 1 with the parabolic concentrator in an upright position. (View A)

FIG. 1 shows an external rear view of the overall invention 100 including the parabolic concentrator reflector 110 along with the novel counterflow heat exchanger receiver tube assembly 200. Parabolic reflector 110 can be selected from a parabolic trough concentrator such as a one manufactured by the Industrial Solar Technology Company water heating system. Parabolic reflector 110 can have an approximate length L, of 20 feet, an overall height, H of approximately five feet(as seen in FIG. 2). Referring to FIG. 1, parabolic concentrator reflector 110 concentrates solar radiation onto a counterflow receiver assembly 200, the latter having an approximate diameter, D, of approximately 2 inches.

Referring to FIG. 1, components 121 through 125 refer to braces and can be formed from metal such as aluminium and the like. Each of the components 121 through 125 can have individual dimensions having approximate cross-sections of one inch by seven and half feet. Components 132 and 134 refer to supports which elevate reflector 110 and its related components by being mounted in the ground 350 by cement and the like. The mount is more clearly shown in FIG. 2. Referring back to FIG. 1, supports 132 and 134 can be formed from metal such as steel, stainless steel and the like, and can have cross-sectional dimensions of approximately two inches by four inches by four feet.

Referring to FIG. 1, component 140 refers to a thermostat assembly incorporating a standard type automotive cooling system thermostat. Thermostat assembly 140 is used to control the flow of water through counterflow receiver tube assembly 200. A serious problem that must be addressed by any water purification system is the effective control of the water temperature to insure that it is truly safe to drink.

Therefore, the water flow rate through counterflow receiver tube 200 must be controlled, especially when the solar energy source is of varying strength. To achieve part of this control, thermostat assembly 140 is located at the end of the receiver tube 200. Thermostat assembly 140 will not allow the flow of liquid therethrough until a specified temperature is achieved. This temperature will be the water disinfection temperature of approximately 180 to 200 F.

Referring to FIG. 1, the flow of infected water 960 into system 100 can be provided by a photovoltaic-powered Direct Current water pump, 190.

FIG. 2 shows an end view 300 of the invention 100 of FIG. 1 in the direction of arrow A with the parabolic concentrator 110 in an upright position in relation to the braces 121,122, 123, 124, 125, and to the supports 132, 134. Counterflow receiver tube 200, located behind thermostat assembly 140 is held by support 132. Parabolic reflector 110 can employ either a conventional manual tracking means- (not shown) such as a handcrank or automatic tracking of the sun using a motor(not shown), as well as conventional tracking techniques with reflector 110 pivoting about pivot point 3 10. Referring to FIG. 1, system 100 can be oriented for East to West tracking in a North to South plane, or system 100 can be oriented for North to South tracking in an East to West plane.

Figure 3:
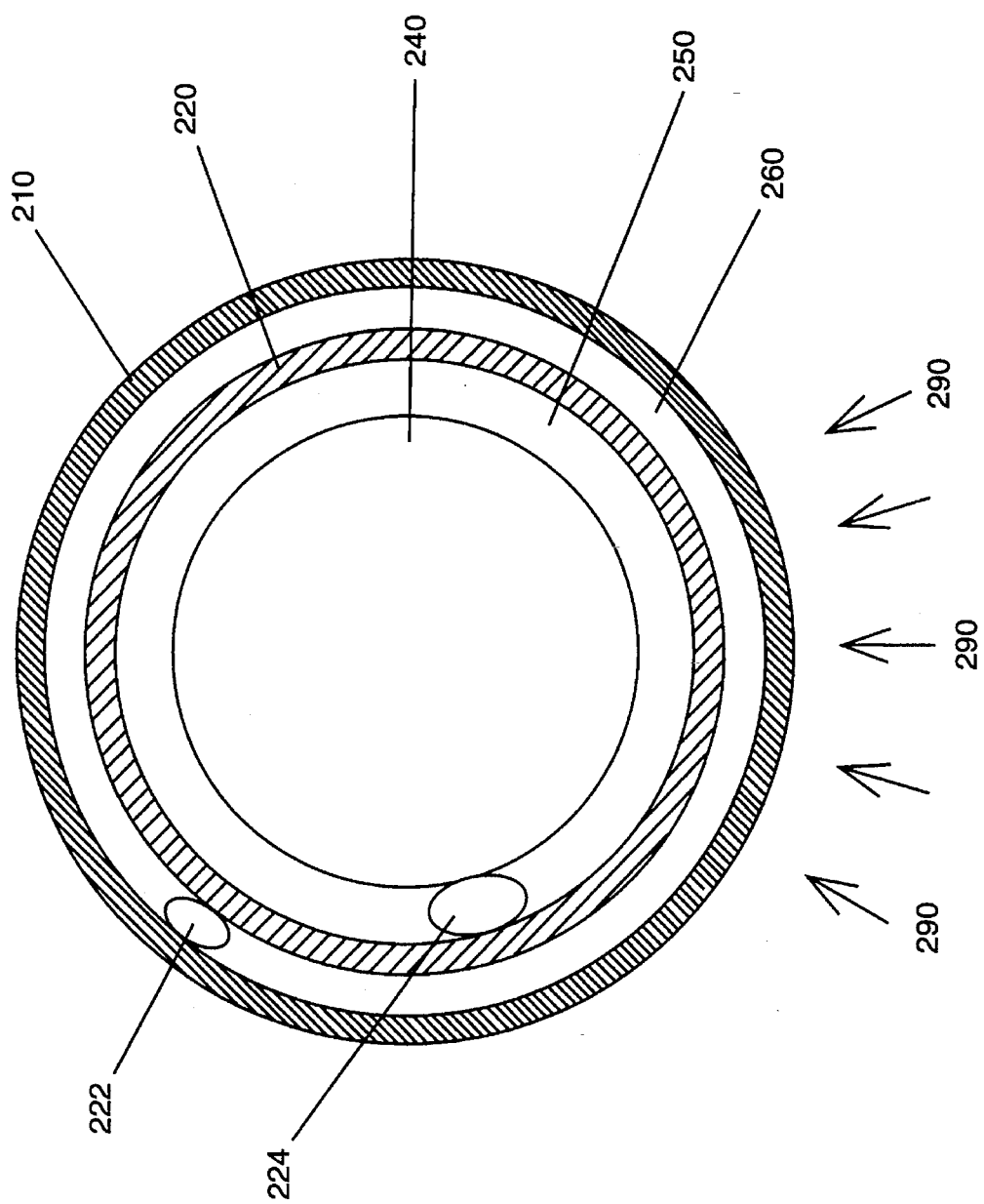
FIG. 3 shows an enlarged cross-sectional view of the counterflow heat exchanger receiver tube of FIG. 1 along arrow B.

FIG. 3 shows an enlarged cross-sectional view of the counterflow heat exchanger receiver tube 200 of FIG. 1 along arrow B. The components of FIG. 3 will now be discussed. Concentric tubes 210 and 220 can be composed of material that has a high thermal conductivity with a resistance to corrosion, such as but not limited to copper and the like. Both spacer 222 and spacer 224 can be a material such as but not limited to copper wire and the like. Spacer 222 can be spirally wrapped around the outer surface of tube 220 for entire length of counterflow receiver tube assembly 200. Spacer 224 can be spirally wrapped around the outer surface of plug 240 for the entire length of counter flow receiver tube assembly 200. The purpose of spacers 222 and 224 is to maintain the spacing for annulus 250 and 260, and to provide water flow spirally around the concentric tube structure for the length of receiver tube assembly 200.

Figure 4:
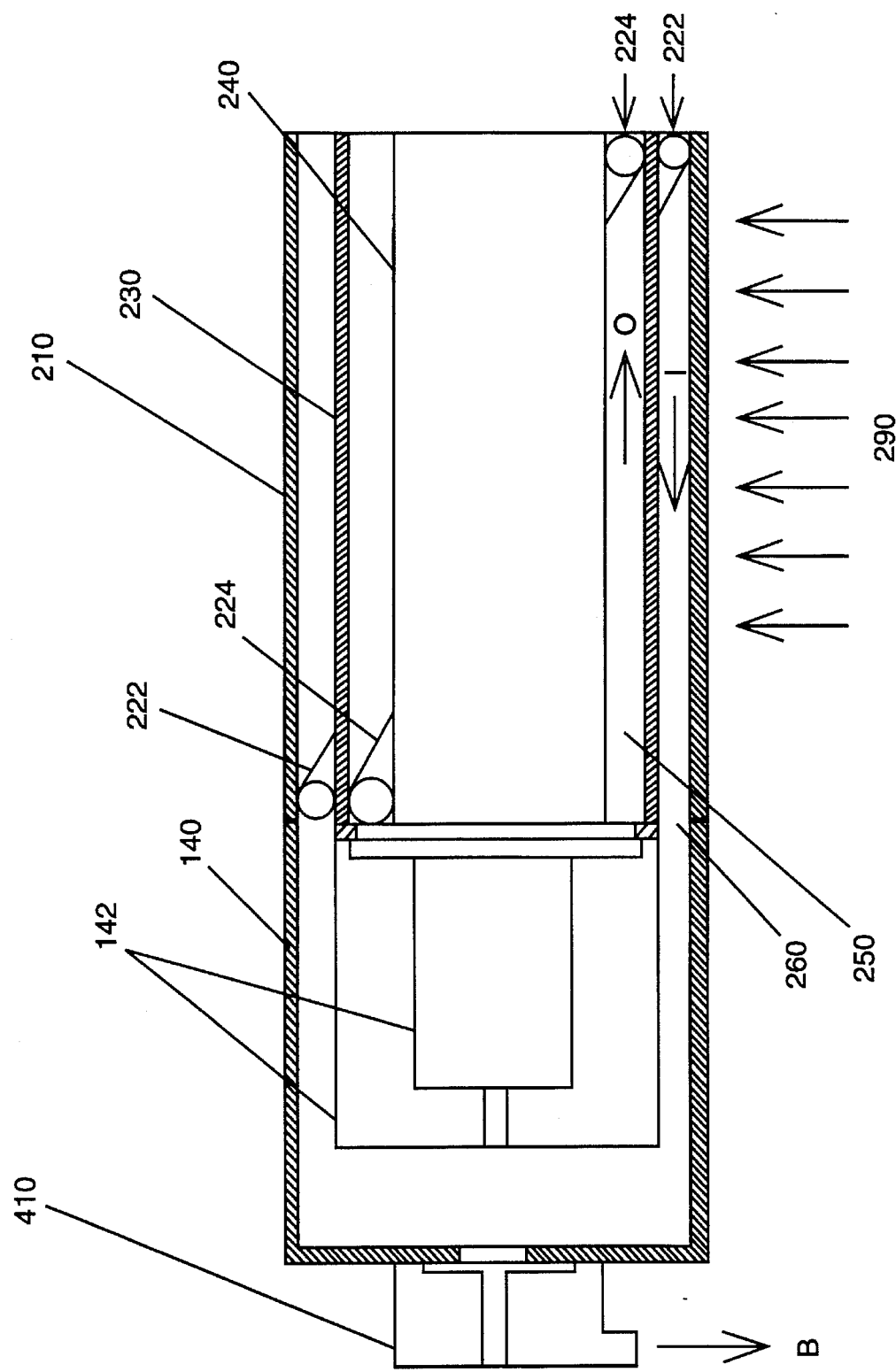
FIG. 4 shows a cross-sectional view of the heat exchanger receiver tube of FIG. 1 along arrow C.

Referring to FIGS. 3 and 4, arrows 290 refer to the concentrated solar flux from the reflector 110 of FIG. 1 or the combustion gases from a fossil fuel burner, to be discussed later in reference to FIG. 5. Component 240 refers to an inner plug formed from material such as but not limited to copper tubing with copper ends and the like.

Referring to FIG. 3, annulus 250 is formed by the space between tube 220 and plug 240. Disinfected return water flow occurs in this annulus which eventually exits to the outside of line 210 of FIG. 1 (910). Annulus 260 is formed by the space between tubes 220 and 210. Infected inlet water flow occurs in annulus 260 eventually passing to the thermostat assembly 140 of FIG. 1. Receiver tube 200 acts as a heat exchanger which uses the outgoing hot disinfected water in annulus 250 to preheat the incoming cold infected water 960 in annulus 260. Using the hot disinfected water to preheat incoming cold water effectively reduces the amount of external energy required to heat the incoming water from ambient conditions to the disinfection temperature. Therefore, the external energy required will be only that which is required to overcome the thermal losses such as the radiation and convection losses to the environment, from tube 210 and the difference between the thermal energy in outlet flow 9 10 and inlet flow 960.

FIG. 4 shows a cross-sectional view through the centerline of the heat exchanger receiver tube assembly 200 and thermostat assembly 140 of FIG. 1 along arrow C. Arrow I refers to incoming water flow and arrow O refers to outgoing water flow. Tube 230 is spirally-wrapped with spacer 222 which causes incoming water flow I to flow spirally around the outside of tube 230 and the inside of tube 210 in annulus 260. Plug 240 is spirally-wrapped with spacer 224 which causes the outgoing water flow O to flow spirally around the outside of plug 240 and the inside of tube 230 in annulus 250. Component 410 refers to a pressure relief valve such as but not limited to a standard automotive radiator cap and the like. Component 142 refers to a thermostat valve such as but not limited to a standard automotive cooling system unit and the like.

In reference to FIGS. 1 through 4, the operation of the components of system 100 will now be discussed. Infected water 960 can come from a stream supply, well supply or the like. Disinfected water 910 can pass outside the system at line 210 and would be ready to be consumed. When sufficient solar energy is available to operate pump 190, two outcomes can occur. One outcome is when thermostat valve 142 is closed, incoming water is blocked from entering annulus 250 thereby eliminating any outgoing flow O. During this outcome, when pump 190 can create sufficient water pressure to overcome pressure relief valve 410, flow B is established which exits the system and is still infected. The purpose of this outcome is to ensure that the hottest possible water created by concentrated solar energy 290 heating tube 210, will flow to the thermostat valve 142 allowing the opening of this valve.

In reference to FIGS. 1-4, the second outcome occurs when thermostat valve 142 is open due to the water in the thermostat assembly 140 being equal to or above the thermostat valve opening temperature. Here, incoming water flow I is allowed to pass into annulus 250 creating outgoing flow O. The spirally counter-current and concentric flows of incoming and outgoing water flows create efficient heat exchange between these two flows. The net result being that outgoing water flow O preheats incoming water flow I. This results in a situation where for a given amount of concentrated solar energy, the value of the incoming water flow rate can be as much as 100 times higher depending upon the effectiveness of the heat exchange between incoming and outgoing water flows, than a conventional system without the internal heat exchange of receiver 200. The system should operate such that pump 190 will create sufficient water pressure at pressure relief valve 410 to create flow B when there is sufficient solar energy to heat the incoming water I to the disinfection temperature when thermostat valve 142 is closed. Further, when thermostat valve 142 is open, pump 190 supplies sufficient flow to maintain as close to the disinfection temperature as possible without oversupplying incoming water which will lower water temperature below the disinfection temperature causing thermostat valve 142 to close.

Referring again to FIGS. 1–4, to supply the concentrated solar energy needed to heat outer tube 210, parabolic concentrator 110 is rotated about pivot point 310 such the focus of the parabolic concentrator 110 is coincident with receiver tube 200. Choosing the appropriate disinfection temperature involves many considerations. Operating with the lowest disinfection temperature will produce the most water output because the thermal losses (radiation and convection) from the receiver tube 210 will be reduced by this lower tube temperature. However, lowering the disinfection temperature from 90 C will require a minimum residence time that increase with lower disinfection temperatures within the counter flow receiver tube assembly 200. This residence time will be determined by the type of organism to be killed (such as but not limited to bacterial, viral, and the like) as well as the temperature profile within tube assembly 200. Therefore, disinfection temperature for this invention will range from approximately 55 C to 90 C

Second Preferred Embodiment

Figure 5:
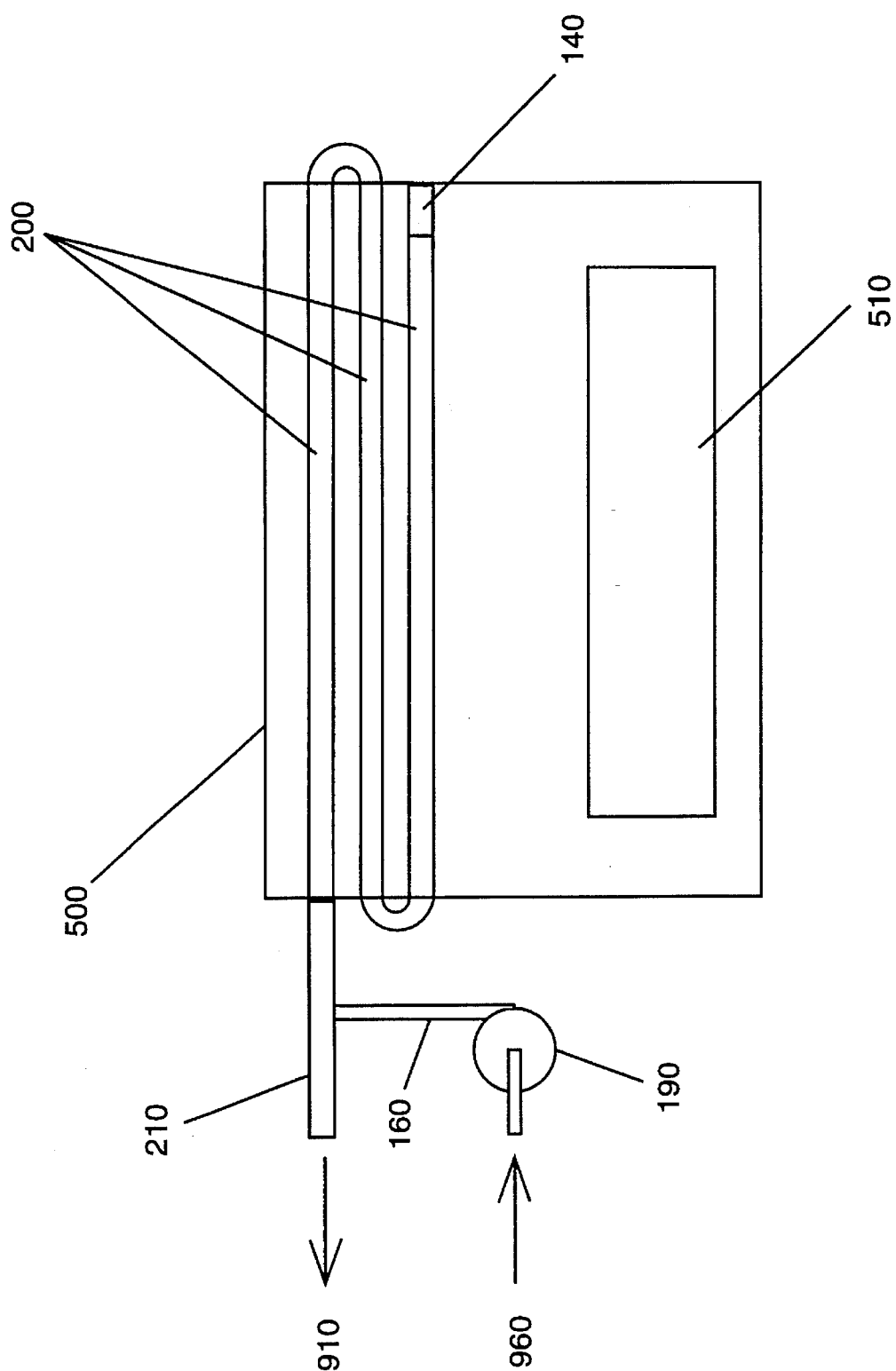
FIG. 5 shows an alternative embodiment using the heat exchanger receiver tube of FIG. 1.

FIG. 5 illustrates an alternative embodiment. This invention has application to energy sources other than solar energy. The counterflow, concentric tube heat exchanger 200 of the above Figures, with external heating ocurring at the outer tube for the purposes of efficiently disinfecting water is also applicable to fossil fuel sources as well. Water-heating tubes of conventional fossil-fueled boilers can be replaced with the counter flow tubes described herein. The principle of operation for the fossil-fuelled embodiment of FIG. 5 is exactly the same as for the solar energy embodiment of FIGS. 1–4, except with several differences.

The geometric configuration of the counterflow receiver 200 of FIGS. 1–4 can now be a series of shorter straight assemblies as typified by the configuration depicted in FIG. 5. In FIG. 5, a conventional boiler 500 with fire box 510 can incorporate the counterflow receiver assembly 200 as shown. For the fossil fuel application of FIG. 5, the outer-tube 210 of the counterflow receiver assembly 200 can include extended surfaces to increase the heat transfer between the combustion gases emanating from 510 and tube 210. Pump 190 can be a photovoltaic-powered pump such as the one described in reference to FIGS. 1–4, or alternatively the pump can be powered by any source of energy that is available when fossil fuel is available, such as but not limited to electrical, gas powered and the like. The pressure relief valve 410 of FIGS. 1–4 will not be required in the fossil-fuel embodiment of FIG. 5. In this embodiment, the thermostat assembly 140 of counterflow receiver assembly 200 does not need to be isolated from the heat source at various times as in the solar energy embodiment of FIGS. 1–4. Thermostat assembly 140 of FIG. 5 does not include the automotive thermostat 142 of FIGS. 1–4. In the embodiment of FIG. 5, thermostat assembly 140 can include but is not limited to a remotely actuated thermostat where a temperature sensing bulb can be located within the counterflow receiver assembly 200 in the same cavity 140 as thermostat 142. The control for this thermostat can alternatively be a water valve at inlet 160, a water valve at outlet 210, or an electrical switch on pump 190.

While the preferred embodiment has been described as being used for disinfecting drinking water, the invention would have other useful applications such as but not limited to disinfecting swimming pool water, therapeutic pool water and the like.

While the two embodiments listed above have described using solar energy, combustion gases and catalysts as the primary heating source, other types of heating sources can be used as long as at least an instantaneous disinfection drinking water temperature is achieved.

Although approximate dimensions and component sizes were described in relation to the above Figures, the sizes of the various components in the system 100 of FIG. 1, can be dictated by the size of the concentrator system desired for water disinfecting benefits and the prevailing weather at the actual site.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An apparatus for disinfecting water comprising:
   an outer tube having a first end and a second end, the first end connected to an incoming water line;
   an inner tube having a first end and a second end, the first end of the inner tube connected to an exit line, and the second end of the inner tube connected to the second end of the outer tube, wherein the inner tube is concentrically located to be substantially within the outer tube;
   means for flowing water from the incoming water line through to the exit line;
   a solar collector for tracking fight, wherein the light substantially heats the outer tube to a water disinfecting temperature range; and
   means to allow the flowing water to pass through the exit line when the disinfecting temperature range is achieved.

2. The apparatus of claim 1, wherein the solar collector includes:
   a parabolic reflector.

3. The apparatus of claim 1, wherein the disinfecting temperature range includes:
   approximately 90 C for instantaneous disinfection.

4. The apparatus of claim 1, wherein the disinfecting temperature range includes:
   less than approximately 90 C when time is adequate to destroy water-borne contaminents.

5. The apparatus of claim 1, wherein the means for allowing the flowing water to pass through the exit fine includes:
   a thermostat valve set to a water disinfecting temperature range.

6. The apparatus of claim 1, further comprising:
   a photovoltaic pump for pumping the water in the incoming water fine.

7. The apparatus of claim 1, wherein the water disinfecting temperature range is adequate for:
   drinking water.

8. The apparatus of claim 1, wherein the water disinfecting temperature range is adequate for:
   pool water.

9. An apparatus for disinfecting water comprising:
   an outer tube having a first end and a second end, the first end connected to an incoming water line;
   an inner tube having a first end and a second end, the first end of the inner tube connected to an exit fine, and the second end of the inner tube connected to the second end of the outer tube, wherein the inner tube is concentrically located to be substantially within the outer tube;
   means for flowing water from the incoming water fine through to the exit line; and
   an artificial heating source for heating the outer tube, wherein the heating source causes the water exiting the exit line of the inner tube to be heated to a water disinfecting temperature range.

10. The apparatus of claim 9, wherein the artificial heating source includes:

combustion gasses.

11. The apparatus of claim 9, wherein the disinfecting temperature range includes:

approximately 90 C for instantaneous disinfection.

12. The apparatus of claim 9, wherein the disinfecting temperature range includes:

less than approximately 90 C when residue time in receiver is adequate.

13. The apparatus of claim 9, further comprising:

a thermostat valve located in the exit line set to a water disinfecting temperature range the thermostat valve allowing water to exit through the exit line when the water disinfecting temperature range is achieved.

14. The apparatus of claim 9, further comprising:

a thermostatically-controlled pump for pumping the water in the incoming water line.

15. The apparatus of claim 9, wherein the water disinfecting temperature range is adequate for:

drinking water.

16. The apparatus of claim 9, wherein the water disinfecting temperature range is adequate for:

pool water.

* * * * *